United States Patent [19]

Park

[11] Patent Number: 5,576,923
[45] Date of Patent: Nov. 19, 1996

[54] APPARATUS FOR GENERATING ANIONS IN VIDEO APPLIANCES

[75] Inventor: Hyun W. Park, Kyungsangbuk-Do, Rep. of Korea

[73] Assignee: LG Electronics Inc., Seoul, Rep. of Korea

[21] Appl. No.: 403,256

[22] Filed: Mar. 10, 1995

[30] Foreign Application Priority Data

Mar. 12, 1994 [KR] Rep. of Korea .................. 94-4914

[51] Int. Cl.⁶ .................................................. H01T 23/00
[52] U.S. Cl. .................. 361/213; 361/229; 361/231; 361/230
[58] Field of Search ................................ 361/212, 213, 361/222, 225, 229, 230–232; 250/324

[56] References Cited

U.S. PATENT DOCUMENTS

| | | | |
|---|---|---|---|
| 3,469,031 | 9/1969 | Setchell | 361/231 X |
| 5,153,811 | 10/1992 | Rodrigo et al. | 361/231 |
| 5,241,449 | 8/1993 | Moeller et al. | 361/231 |

FOREIGN PATENT DOCUMENTS

| | | |
|---|---|---|
| 156930 | 6/1954 | Australia . |
| 2452824 | 5/1976 | Germany . |
| 392873 | 5/1933 | United Kingdom . |

Primary Examiner—Fritz M. Fleming
Attorney, Agent, or Firm—Helfgott & Karas P.C.

[57] ABSTRACT

The present invention releases anions out of a main body, by using convection occurring due to heat from heat elements inside a product. According to this invention, an apparatus for generating anions is positioned at the upper part in a main body, an ascending air stream formed by heat from heat elements which are in the lower part of a product pushes anions out of a product. Thus an extra fan and fan driver are unnecessary.

1 Claim, 3 Drawing Sheets

APPARATUS FOR GENERATING ANIONS IN VIDEO APPLIANCES

BACKGROUND OF THE INVENTION

1. Field of the Invention

The present invention relates to an apparatus for generating anions in video appliances. More specifically the present invention relates to an apparatus for generating anions, which releases anions out of a main body of a product, using convection occurring by heat from heating elements.

2. Description of the Related Art

When using video appliances, such as a television receiver, a computer monitor, an audio/video system, etc., several people usually use them in a limited space. Thus, environmental problems arise from their use. That is, the users are exposed to an environment tainted with problems, such as dust, air pollution, cigarette smoke or the like.

Meanwhile, recent-developed video appliances, having an apparatus for generating anions, create and release anions simultaneously with performing their own functions, so that the environment can be improved.

The conventional video appliances having an apparatus for generating anions, adopt an exhaust fan in order to release anions out of their body. This is the so-called forced blowing method.

However, such a method results in other problems.

One is fan noise which creates another environmental problem.

Another is the necessity of the addition of extra components and circuitries for driving the fan, as well as the addition of a fan. The additional components make it difficult to make the best of the interior space of a product. This is also contrary to the growing tendency to miniaturize products.

Finally, the cost that is spent on ancillary functions instead of primary functions will be increased. Aside from the increased cost of production of the components being added, it increases power consumption, design cost, manufacturing cost, etc.

SUMMARY OF THE INVENTION

It is an object of the present invention to provide an apparatus for generating anions in video appliances, which releases anions out of a main body of a product, utilizing convection caused by heating elements or heat sinks rather than an exhaust fan.

Therefore, this invention not only achieves the above object but avoids the problems described previously.

In accordance with one aspect of this invention, there is provided an apparatus for generating anions in video appliances, comprising:

means for generating a high voltage;

means for creating anions, utilizing the high voltage generated from the means for generating a high voltage; ,and means for holding and supporting the means for creating anions, and for releasing the anions out of a main body, utilizing convection occurring by heat from heating elements.

These and other objects will appear upon reading the following specification and claims and upon considering in connection therewith the corresponding attached drawing.

BRIEF DESCRIPTION OF THE DRAWINGS

In the drawings in which a preferred embodiment of the present invention is disclosed.

DETAILED DESCRIPTION OF THE PREFERRED EMBODIMENT

As known to all, an anion is a general term regarding everything charged with negative electricity, from electron particles to floating matters possessing a diametral size.

There has been several studies on the physiological functions and efficacies of anions. These studies have revealed some efficacies, such as nervous tranquilization, hypnotic alleviation of pain, stirring refreshment, improvement of appetite, relieving nervous fatigue, delaying senescence, etc.

Figure 1:
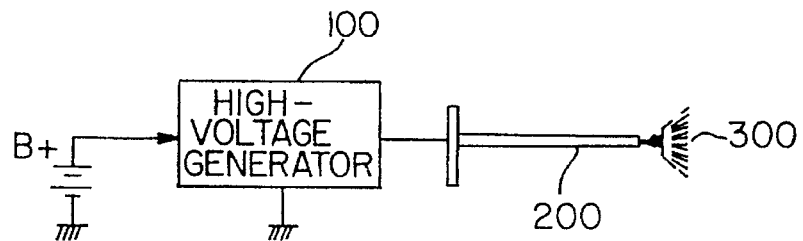
FIG. 1 shows a constructional diagram of an apparatus for generating anions.

As to creation of such anions, referring to FIG. 1, a high-voltage generation circuit 100 makes a high voltage of an input DC voltage (B+), and the high voltage is applied to a discharge needle 200 so that a corona discharge into the air is accomplished. The air is ionized by such a discharge, and a large amount of anions 300 is generated.

Figure 2:
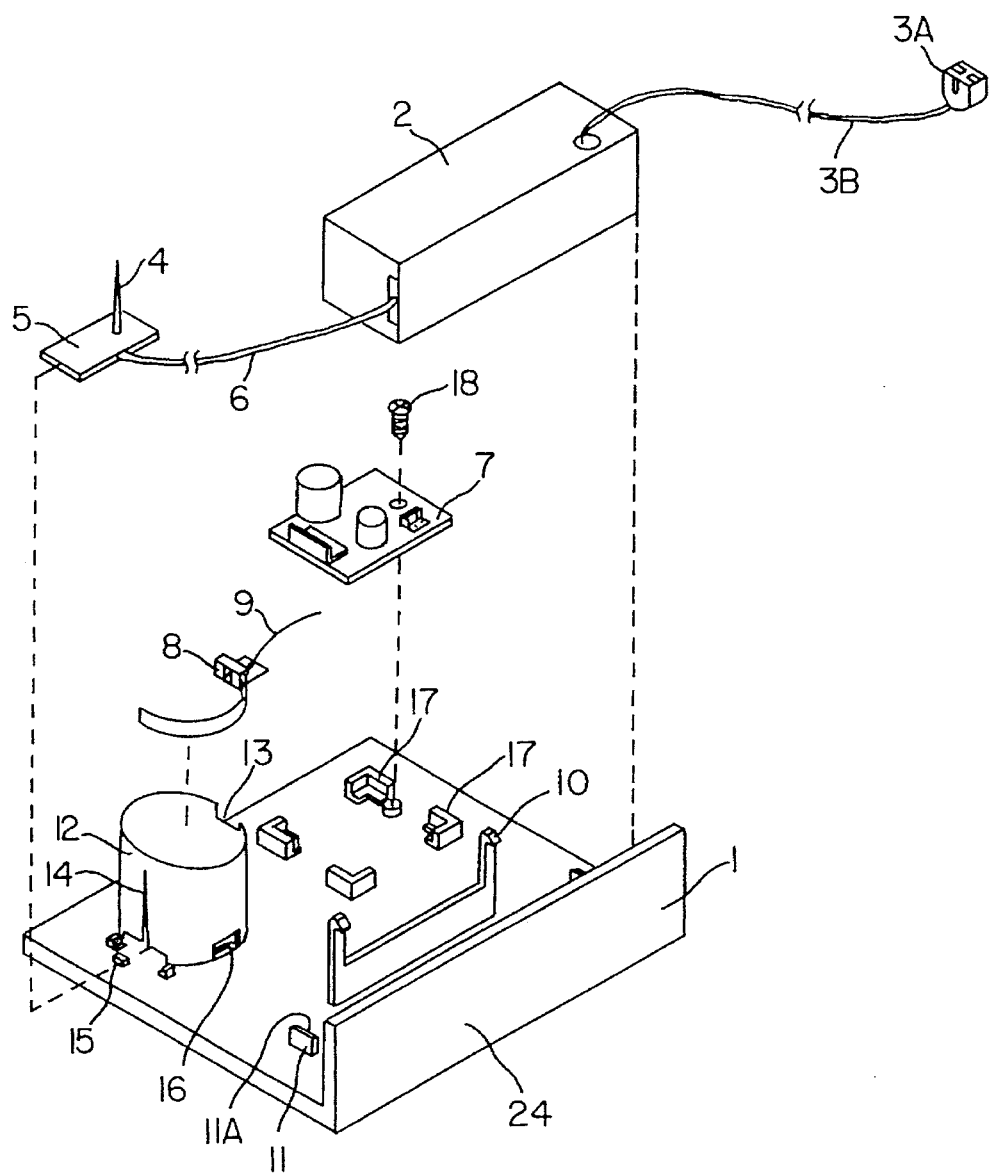
FIG. 2 is a view in perspective of the apparatus according to the present invention.
Figure 4:
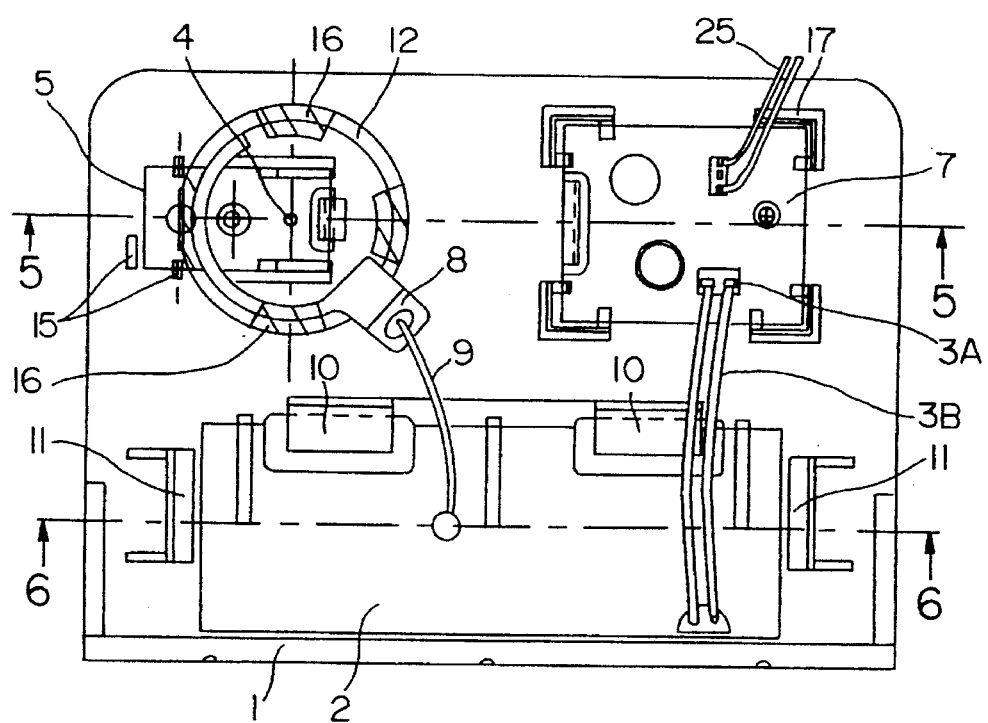
FIG. 4 is a plane view showing the apparatus according to the present invention.

An apparatus for generating anions in video appliances according to the present invention is depicted in FIG. 2 and FIG. 4.

With reference to FIGS. 2 and 4, this invention generally comprises a base 1 for supporting a whole apparatus and a high-voltage generator 2 being mounted on the base.

A connector 3A and a cord 3B for feeding a source voltage are attached to the high-voltage generator 2. A discharge needle 4 mounted on a discharge needle board 5 is connected to the high-voltage generator 2 through a cord 6.

A protection circuit board 7 is also mounted on the base 1, playing a part in inhibiting the high voltage from leaking into a power source end.

A discharge pole 8 is provided, confronting the discharge needle 4. The discharge pole 8 is grounded to a chassis of the high-voltage generator 2 with a cord 9.

On the base 1, the high-voltage generator 2, the protection circuit board 7, and the discharge pole 8 are mounted.

Figure 6:
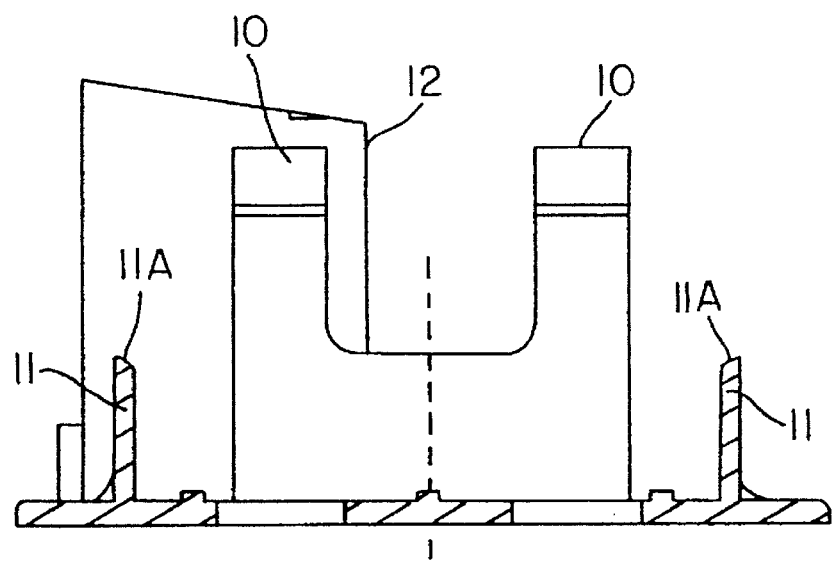
FIG. 6 is a section upon the line 6—6 of FIG. 4.

An elastic hook 10 for holding the high-voltage generator 2 is mounted also on the base 1. A supporting plate 11 is mounted also on the base 1, which fixes, cooperating with the elastic hook 10, the high-voltage generator 2 to its regular position on the base 1. The Supporting plate 11 has, as shown in FIG. 6, a slope 11A at the tip thereof in order that the high-voltage generator 2 can easily be equipped.

Pushing the high-voltage generator 2 into the space constituted with the elastic hook 10 and the supporting plate 11, the high-voltage generator 2 slides down along the slope 11a and is safely fixed by the elasticity of the elastic hook 10.

A releasing barrel 12 holding and supporting the discharge needle 4 and the discharge needle board 5 are mounted on the base 1. It is desirable that the releasing barrel 12 is cylindrical. It may protect the user, holding the discharge needle therein, from receiving an unexpected electric shock.

A groove 13 is formed at the upper part of the releasing barrel 12, and the discharge pole 8 is fixed to the groove 13. It is desirable that the discharge pole 8 forms a shape of a semicircle or a circle and is attached to the inner face of the barrel.

A notch 14 provided at the lower part of the releasing barrel 12 makes it possible to insert the discharge needle 4 into the barrel. On the base below the notch 14, supporting ribs 15 which support the discharge needle board 5 are prepared.

At the lower part of the releasing barrel 12, an air inlet 16 is formed. Into this air inlet 16, an ascending air stream flows, which is formed by heat radiated from heating elements inside a main body.

Supporting ribs and bosses 17 are installed also on the base 1. The protection circuit board 7 is held and supported by these ribs and bosses 17 and a screw 18.

Figure 3:
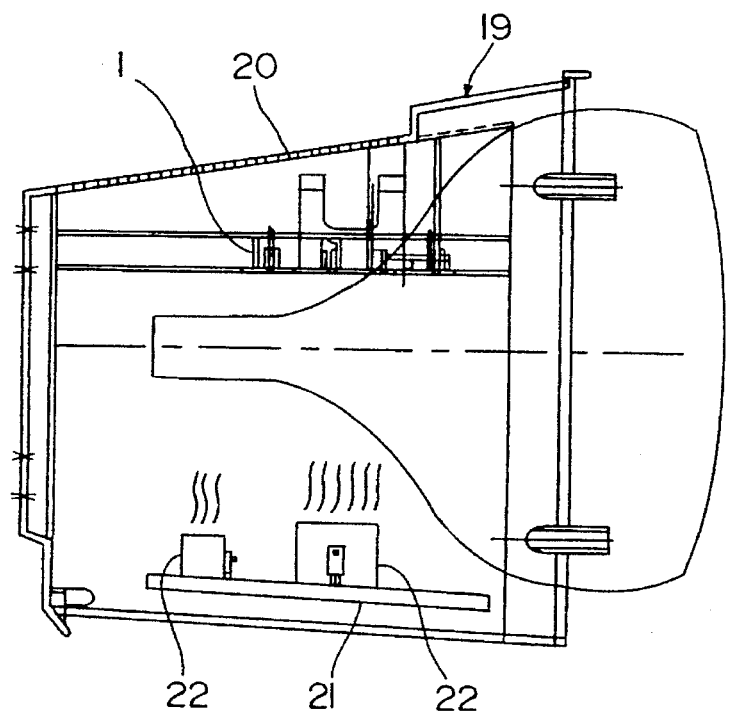
FIG. 3 is a sectional view showing a computer monitor adopting the apparatus according to the present invention.
Figure 5:
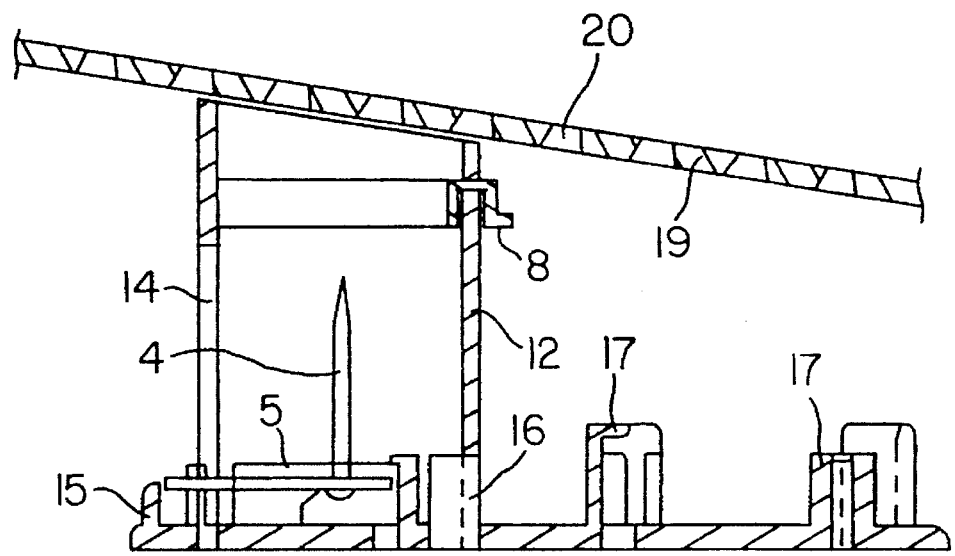
FIG. 5 is a section upon the line 5—5 of FIG. 4.

FIG. 3 is a sectional view showing a computer monitor adopting the apparatus for generating anions constructed as above, FIG. 5 and FIG. 6 are sections upon the line 5—5 and 6—6 of FIG. 4, respectively.

As shown in FIG. 3, the base 1, on which the aforementioned high-voltage generator 2, protection circuit board 7, and discharge needle 4 are mounted, is assembled beneath a top cover 19.

In such a structure, as shown in FIG. 5, since the upper opening of the releasing barrel 12 borders ventilating holes 20 of the top cover 19, the anions created in the releasing barrel 12 can be released out of the main body.

Specifically, in order to utilize convection occurring by heat radiated from heating elements 22 among elements mounted on a main circuit board 21, the base 1 is installed over the heating elements 22. Thus an ascending air stream penetrates from the air inlet 16 to the upper opening of the releasing barrel 12, with anions.

Referring to FIG. 4, when a power source is supplied to a main system, it is fed through a power cord 25 to the protection circuit board 7. From the protection circuit board 7, a DC voltage is applied through the connector 3A and cord 3B to the high-voltage generator 2. The high-voltage generator 2 makes, as shown in FIG. 1, a high voltage-of the DC voltage and applies the high voltage to the discharge needle 4 through the cord 6.

The discharge needle 4 performs a corona discharge with the discharge pole 8 so that the air around them is ionized. Anions are accordingly created.

The anions are released from the upper opening of the releasing barrel 12 through the ventilating holes 20 of the top cover 19 out of a main body. The released anions mixed with the air are gradually diffused in a room.

As the main system works, the heating elements 22 on the main circuit board 21 radiates heat, the heat forms an ascending air stream. The ascending air stream enters the releasing barrel 12 through the air inlet 16 positioned at the lower part of the releasing barrel 12, and pushes the anions out of the releasing barrel 12.

Such an operation continues as long as the main system works, i.e., as long as the heating elements radiates heat.

Although the number of anions created in the releasing barrel 12 is small, they can sufficiently be released out of the releasing barrel 12 by convection occurring by heat radiated from the heating elements.

It is preferable to use an ABS resin or an epoxy for the cover 19 rather than PVC. Because the former is superior to the latter in insulation, the anions are less electrodeposited on the inner face of the cover, In efficacy, when using a video appliance, such as a television, a computer monitor, etc., this invention provides a pleasant environment to a user through anions released by convection inside a main body. Such an efficacy is obtained even without an extra fan and fan driver.

What is claimed is:

1. An apparatus for generating anions in video appliances, comprising:

means for generating a high voltage;

means for creating anions by said high voltage generated from said high voltage generating means; and means for releasing anions created by said anion creating means out of a main body by using convection caused by heat radiated from heating elements provided in said main body, wherein said anion releasing means receives and supports said anion creating means therein, and wherein said anion releasing means comprises an air inlet formed at the lower part of said anion releasing means and an opening formed at the upper part of said anion releasing means and being opposite to ventilating holes formed on said main body.

* * * * *